(12) United States Patent
Glaser

(10) Patent No.: US 6,652,101 B1
(45) Date of Patent: Nov. 25, 2003

(54) METHOD AND APPARATUS FOR PERFORMING VISION SCREENING

(76) Inventor: Stephen R. Glaser, 101 Lakeforest Blvd., Suite 380, Gaithersburg, MD (US) 20877

( * ) Notice: Subject to any disclaimer, the term of this patent is extended or adjusted under 35 U.S.C. 154(b) by 51 days.

(21) Appl. No.: 09/972,044

(22) Filed: Oct. 9, 2001

(51) Int. Cl.$^7$ ................................. A61B 3/02
(52) U.S. Cl. ..................................... 351/239
(58) Field of Search ............................... 351/237, 239, 351/240, 241, 242, 243, 244, 222, 223, 224

(56) References Cited

U.S. PATENT DOCUMENTS

| | | | |
|---|---|---|---|
| 1,990,218 A | | 2/1935 | Bailey |
| 4,421,392 A | * | 12/1983 | Pitts Crick et al. ......... 351/224 |
| 4,968,131 A | | 11/1990 | Lewis |
| 5,061,059 A | | 10/1991 | Horn |
| 5,436,681 A | * | 7/1995 | Michaels .................... 351/240 |
| 6,244,713 B1 | | 6/2001 | Hayashi |
| 6,406,147 B1 | | 6/2002 | Hayashi et al. |

FOREIGN PATENT DOCUMENTS

| | | |
|---|---|---|
| EP | 02/32189 | of 0000 |
| FR | 2 621 474 | 4/1989 |
| WO | PCT/US02/32189 | of 0000 |

OTHER PUBLICATIONS

Hohmann et al. "Die validierung eines neuen Sehscharftests (H–Test) fur Vorschulkinder", Spektrum Augenheilkd, vol. 4, No. 6, 1990, pp. 240–244.

Graf et al. "Sehscharfenbestimmung mit LH–Symbolen und Landoltringen" Spektrum Augenheikd, No. 215, 1999, pp. 86–90.

* cited by examiner

Primary Examiner—George Manuel
(74) Attorney, Agent, or Firm—Shaw Pittman LLP

(57) ABSTRACT

The present invention relates to a vision screening system and a method for using the system to easily perform screenings for vision disorders, including amblyopia in children using only one examiner. The system includes a lightweight, portable apparatus having a surface upon which a series of images are imprinted, projected, or digitally altered. The size, shape, appearance, arrangement, and quantity of the images are chosen to allow an examiner to rapidly screen the examinee for a visual disorder such as amblyopia. The apparatus also includes a measurement tool, integrated with the apparatus, which enables the examiner maintain the surface of the device at a predetermined distance from the examinee's eyes. To screen a child's vision, the apparatus is positioned at a predetermined distance from the examinee's eyes using the systems built-in measuring distance device. With one eye covered at a time with adhesive patches provided as part of the vision screening system, the examinee is asked to either identify an image displayed on the apparatus, or point to a matching image on a card provided as part of the system, that is located at a close distance to the examinee. Based upon the examinee's collective responses, the examiner can determine whether the examinee is affected by a visual disorder such as amblyopia. The entire system (the optotypes target apparatus with built-in measuring device, matching optotypes card, adhesive eye occluders, and instructions) are all provided in a self-contained, small, lightweight box or package for ease of transport and storage.

19 Claims, 8 Drawing Sheets

METHOD AND APPARATUS FOR PERFORMING VISION SCREENING

FIELD OF THE INVENTION

The present invention relates to visual screening systems and methods, and more particularly, to a method and apparatus screening monocular visual acuity to detect vision disorders, such as amblyopia.

BACKGROUND INFORMATION

It is recommended to screen children at an early age for vision disorders. The American Academy of Pediatrics, along with other medical professional organizations, recommend that children have their visual acuity quantified at least by age four. In many instances, it may be possible to correct a child's vision if problems are detected during early childhood.

Amblyopia is the leading cause of reversible blindness in children in the United States, affecting approximately 2–4% of the population. In order to successfully treat amblyopia, a child must be diagnosed with this condition at an early age. If the condition is detected sufficiently early, it is often possible to completely, or at least substantially, correct the child's vision. However, if left untreated by seven to nine years of age, it may only be possible to slightly improve a child's vision, if at all.

Amblyopia, also known as "lazy eye," is a condition in which a patient's brain processes substantially more visual information from one eye than the other, such that the patient is only "seeing" with one eye. This typically develops during early childhood, when a child compensates for reduced vision in one eye by neurodevelopmentally learning to see only through the other eye. Amblyopia may result from a misalignment of a child's eyes, known as "crossed eyes." Amblyopia can also be caused by a marked difference in visual acuity between a child's eyes, causing the child to focus through only one eye. This is called anisometropic amblyopia. For more information about amblyopia, see http://www.preventblindness.org/children/amblyopiaFAQ.html.

If detected at an early age, the debilitating effects of amblyopia may be avoided in many circumstances by training a child's visually immature brain to process images from the affected eye. The amblyopic eye is commonly treated by using a patch to cover a patient's "stronger" eye, which forces the patient to use the weaker eye. Another alternative method to "patching" is to use eye drops to "blur" the vision in a child's stronger eye. For a patient with anisometropic amblyopia, who is unable to see normally through one or both eyes due to an uncorrected refractive error, proper spectacle correction (glasses) is also prescribed to be worn full time, simultaneously with the "patching" or "blurring" treatment, to focus the blurred image on the retina of the affected eye (at the back of the eye). The use of the patch, or eye drops, is gradually tapered off, usually over the course of several months or even years, depending upon the severity of the problem.

Unfortunately, it can be difficult to diagnose vision disorders such as amblyopia in children of early age. A child may not realize, or otherwise not be able to communicate, that the child's eyesight is outside of a normal range. A child with normal vision in one eye may not notice a vision problem, even if the child's other eye is severely visually impaired. Parents are also often unable to detect that a child is suffering from a vision disorder. For example, although a child with anisometropic amblyopia may be legally blind in the affected eye, the condition often may be overlooked because the child's eyes are properly aligned, and so the child may not appear to be having vision difficulties.

There are several methods and systems that presently exist for examining a child's vision. Assessing monocular visual acuity (checking visual acuity in one eye at a time) is the best indicator of amblyopia. Monocular visual acuity assessment is the best indication of any eye pathology in children of pre-school age.

The most common method of screening vision in children of pre-school age is through the use of an eye chart. This is typically performed by positioning a wall chart across a room, at least ten feet from a child to be examined. An examiner points to optotypes (letters or symbols) that are displayed on the chart while the child covers one eye with her hand or some other type of cover. To reliably test the child's vision in one eye at a time, an adhesive patch may be used to ensure the child does not try to compensate for poor vision in one eye by "cheating" with the other eye. If the test indicates that the child can see much more clearly from one eye than the other eye, then the child may be suffering from amblyopia.

Although a vision chart can be an effective tool for measuring visual acuity, there are several disadvantages to its use for screening pre-school aged children for vision disorders. First, wall charts are not easily portable and require a special room or hallway to use. Secondly, a second examiner is usually required when using a vision chart if the child is too young to read letters or describe the appearance of the "optotype" symbols, or if the child otherwise cannot verbalize the correct response due to shyness or lack of understanding of the test. As one examiner stands at the chart and points to certain optotypes (symbols) on the chart, the second examiner holds a second chart at a closer proximity to the child. The second chart contains the same optotypes, but in a different arrangement. With one eye covered at a time, the child points to the optotypes on the second chart that correspond with the optotypes that the first examiner points to on the first chart. The second examiner is needed to monitor the child's responses while simultaneously monitoring the child to detect squinting or if the child is otherwise "cheating" on the vision exam.

A photoscreener can also be used for detecting vision disorders in very young children. A portable camera (such as the MTI PhotoScreener, by Medical Technology and Innovations, Inc., of Lancaster, Pa.) takes a photograph of a child's eyes. In the photographs, strabismus (misalignment of the eyes) and conditions that lead to amblyopia such as astigmatism, cataracts and refractive errors show up as crescents on the child's pupils. A photoscreening test is quick, noninvasive and painless, and may be useful as a high-volume initial screening method in schools. However, most photoscreeners that are presently available provide many false results (both false negatives and positives), and are not reliable for predicting visual acuity. Photoscreeners also require subsequent film processing, and may be too expensive to be used by primary care physicians or parents.

An electronic vision screener is another device that is available for performing children's vision screening. To use a vision screener (such as the Titmus Vision Screener), a child peers into a portable box and is asked to identify optotypes that are displayed on a screen in the box. Using a separate controller, an examiner can control the display of the optotypes on the screen. A vision screener can be used to test for acuity (near and far), depth perception, color perception, muscle balance (lateral and vertical phoria), and horizontal visual fields (peripheral vision of 130 degrees in each eye).

While these electronic vision screeners can be useful for screening adults' vision (and are commonly used as part of a driver's exam by local departments of motor vehicles), there are several disadvantages to using the device for screening children's vision for disorders, such as amblyopia. To use a vision screener, the child is required to recognize and identify the optotypes displayed on the screen by speaking aloud, which may not be possible for young children (as opposed to matching optotypes from an image to an optotype card). The mirrors and lighting in the device may confuse a young child, and generate less accurate results. In addition, although the device is designed to be able to separately measure the visual acuity in each eye, a young child with poor vision in one eye may shift his head to read the optotypes with the better seeing eye, and thus the amblyopic eye will not be identified. Finally, electronic vision screeners are expensive to buy and repair and are not easily portable.

Although it cannot be used to screen for vision disorders, an autorefractor (such as the SureSigh™ Autorefractor by Welch Allyn, Inc.) can also be used to perform objective refraction of a child's eyes. The child is instructed to look at a light emitting from the device, while the physician adjusts the device to focus the lens at the child's eyes, one at a time. The autorefractor then measures the prescription of each eye. Generally, autorefractors are only accurate when used with children after the child receives eye drops (cycloplegia) to dilate the child's pupils and temporarily inhibit the child's strong focusing mechanism. The use of eye drops for screening purposes can become impractical, and children are generally intolerant to the delivery of eye drops for pupil dilation. In any case, an autorefractor only measures the physical characteristics of a child's eyes, and cannot indicate whether the child has a vision disorder such as amblyopia. Finally, the cost of an autorefractor renders its use prohibitive to most primary care physicians or parents.

If a child who is diagnosed with amblyopia is to be treated by "blurring" the child's stronger eye with eye drops, the child may need to be examined to determine the proper dosage of eye drops that is required to adequately "blur" the child's vision. One method of performing this examination is known as the Near Acuity Test (manufactured by PrecisionVision™, La Salle, Ill.) developed by the Pediatric Eye Disease Investigator Group ("PEDIG"). To perform this test, a physician first places eye drops in the child's stronger eye and occludes the weaker eye. The physician then uses a portable flip chart apparatus as shown in FIG. 1 to test the child's vision in the strong, but medically "blurred eye" at near distances. If the child is able to see items that are displayed on the chart, there is an indication that the child's stronger eye is not being adequately "blurred" by the eye drops to treat amblyopia.

The child is shown a series of cards 10 on the flip chart 11 of FIG. 1, one at a time, and is asked to identify what is displayed on each card. During the examination, the cards are maintained at a close distance to the child, approximately eighteen inches from the child's eye. A string 12 measuring 40 cm (0.4 meters) in length is also attached to the base of the flip chart 13. Using the string, the physician can easily measure the distance between the cards and the child's eye, and hold the flip chart at a certain distance from the child. The physician can use the string to periodically re-measure the distance between the child and the chart to maintain a constant distance during the examination.

As shown in FIG. 1, the cards each display one of the letters 14 "H", "V", "O", or "T", which are commonly-known optotypes for measuring visual acuity. The optotypes that are displayed on the cards in the flip chart are arranged in a progression of increasingly smaller sizes, which are calibrated 15 to provide an indication of visual acuity (e.g., 20/400, 20/200, 20/100, 20/50, 20/30, etc.) according to the 40 cm distance between the card and the child's eye. If the child is able to read the alphabet and is also able to see the optotype on the chart, then the child can respond by simply speaking aloud the correct letter that is displayed on each card. For children who cannot read or speak, the base of the flip chart also provides a separate display 16 of the letters "H", "V", "O", and "T" in a much larger font. Instead of speaking aloud, the child can point to a letter displayed in the large text that matches the letter displayed on the card. Because the card is maintained at a distance of only 40 cm from the child's eye, the child should be able to point to and reach the base of the card. However, as it may be difficult for the child to properly point to these optotypes without moving closer to them, the child may be continually moving, it becomes difficult to maintain the 40 cm distance between the cards and the child's eyes.

Although the Near Acuity Test can assist a physician in determining the proper dosage of eye drops in the known strong eye for effectively treating amblyopia, this test cannot be used to screen for and diagnose vision disorders, such as amblyopia. The test is designed to examine a child's vision only at close distances, because it is only necessary to "blur" the child's vision at a close distance to cause the child to begin using the weaker eye. Accordingly, the test is specifically designed to test a child's "near acuity" in the strong eye at a distance of approximately 40 cm from the child's eye. The string that is attached to the base of the chart is 40 cm in length and the optotypes on the cards are calibrated and sized to be viewed at that distance. In contrast, it is necessary to test a child's vision at a longer distance to screen for amblyopia. The Near Acuity Test is intended to assess a decline of near acuity from medically inhibiting a normal eye focusing mechanism. It is not intended to screen for amblyopia. Finally, the selection of vision levels in the Near Acuity Test for providing an indication of visual acuity (e.g., 20/400, 20/200, 20/100, etc.) is not sufficient for screening vision for vision disorders such as amblyopia.

Accordingly, there is a need for a method and system for screening a child's vision to detect vision problems, such as amblyopia, that manifest in early childhood. Because children's vision is typically screened during periodic visits at a primary care doctor's office and through school vision screens, as opposed to examinations by optometrists or ophthalmologists, the method and system should be inexpensive, uncomplicated, and easily performed by a primary care practitioner, a school nurse, or even a parent. Furthermore, since children often have a short attention span and are sensitive to physical discomfort, the method and system should be quick, noninvasive, and painless.

For many of the same reasons that it is difficult to perform vision screening of pre-school aged children, challenges also exist when performing vision examinations of others, such as mentally challenged individuals or individuals suffering from any form of communication disorder, including stroke, throat trauma, or other extreme illness. Therefore, there is also a need for a method and system for quickly assessing visual acuity with a portable device in any individuals from whom subjective responses are difficult to elicit.

SUMMARY OF THE INVENTION

The present invention relates to a vision screening system and a method for using the system to perform screenings for vision disorders, including amblyopia in children. The system includes a lightweight, portable apparatus having a surface upon which a series of images are imprinted, projected, or digitally altered. Adhesive patches or other devices to occlude one eye are included. The items are packaged in a small, lightweight container that facilitates ease of transport and storage. The size, shape, appearance, and arrangement of the images on the portable apparatus are chosen to allow an examiner to detect an examinee's visual acuity. The images on the surface of the apparatus may include letters of the alphabet or symbols, known as optotypes. The apparatus also includes a measurement tool, integrated with the apparatus, which enables the examiner to maintain the surface of the device at a predetermined distance from the examinee's eyes. In one embodiment of the present invention, the system may additionally include a separate card containing images that match the images on the surface of the apparatus.

To screen a child's vision, the apparatus is positioned at a predetermined distance from the examinee's eyes. One or more optotypes are displayed on the surface of the apparatus. With one eye covered at a time, for example, by using adhesive patches, the examinee is asked to either identify an optotype displayed on the apparatus, or point to a matching optotype on a card that is located at a close distance to the examinee. Depending upon the examinee's responses, the examiner then selects optotypes of different sizes to display on the surface of the apparatus for the examinee to identify. Based upon the examinee's collective responses, the examiner can determine whether the examinee is affected by a visual disorder.

It is an object of the present invention to provide a method for conducting a vision examination by an examiner to screen a patient for vision disorders. A set of display cards are held at a predetermined distance from the patient's eyes. Each display card contains an optotype of a size calibrated for display at the predetermined distance, and the optotypes are of different sizes to provide an indication of visual acuity at one of a plurality of particular vision levels. For each display card, the patient is requested to find an optotype on a reference card that matches the displayed optotype. The reference card is positioned within close proximity to the patient. A correct match indicates that the patient is able to see the optotype on the display card.

It is another object of the present invention to provide a method of conducting a vision examination by an examiner to screen a patient for vision disorders. A predetermined distance from the patient is measured. A set of display cards is held at the predetermined distance from the patient, wherein each display card contains an optotype of a size calibrated for display at the predetermined distance, and wherein the optotypes are of different sizes to provide an indication of visual acuity at one of a plurality of particular vision levels. A display card is selected from the set of display cards. The selected display card is displayed and the patient is requested to identify the optotype on the display card. An attempted identification of the optotype is received from the patient. Additional display cards are selected and displayed, and the patient continues to attempt to identify the optotypes on the cards, until either the patient is unable to identify at least a predetermined number of optotypes on display cards, or a sufficient number of optotypes have been identified by the patient to screen the patient for a particular vision disorder.

Another object of the invention is to provide a vision screening apparatus for use by an examiner for screening vision in a patient to detect vision disorders. The apparatus includes a display medium for displaying optotypes of varying sizes, calibrated to indicate an assessment of visual acuity, wherein the display medium is positioned at a predetermined distance from the patient. The apparatus further includes a reference card that displays a set of optotypes corresponding to the optotypes provided on the display medium, positioned at a close distance from the patient to enable the patient to indicate which optotype on the reference card matches the optotype displayed on the display medium. This enables the examiner to determine whether the patient is able to see the optotype on the display medium. The predetermined distance that the display medium is positioned from the patient is at least a minimum distance from the patient to measure distance vision, but is less than a maximum distance by which the examiner can be in close proximity to both the display medium and the reference card.

It is also an object of the present invention to provide a portable vision screening apparatus for use by an examiner for screening vision in a patient to detect vision disorders, comprising a series of display cards attached to a base as a flip chart, wherein each card displays an optotype calibrated to indicate an assessment of visual acuity at a particular vision level when viewed from a predetermined distance. A string is attached to the base of length equal to the predetermined distance. The predetermined distance from which the display cards are to be viewed is of at least a minimum length to measure distance vision to enable detection of vision disorders.

DETAILED DESCRIPTION OF THE INVENTION

According to an embodiment of the present invention, a compact, portable vision screening apparatus is used to screen pre-school aged children for vision disorders, such as amblyopia. The apparatus includes a flip chart of display cards and a string of a predetermined length. An optotype, such as a letter or a symbol, is imprinted on each card. The cards are arranged in the flip chart in a progression of increasingly smaller sizes, calibrated to provide an assessment of visual acuity (e.g., 20/100, 20/50, 20/30, etc.)

according to a predetermined distance between the chart and the child's eye when in use. The passing acuity of 20/30 has been specifically determined to effectively eliminate the possibility of significant amblyopia in the tested eye. A separate reference card is provided with optotypes that match those displayed in the flip chart. The portable vision screening apparatus is lightweight, compact, inexpensive to manufacture, and easy to use.

In use, an examiner holds the apparatus at a predetermined distance from the child, according to the length of the string that is connected to the apparatus. With one eye covered at a time, the child is asked to identify the optotype that appears on each card. If the child is unable to read or speak aloud, the child is then asked to find the matching optotype on the reference card, which the child holds in his lap. Based upon the child's responses, the examiner can screen for amblyopia.

Figure 1:
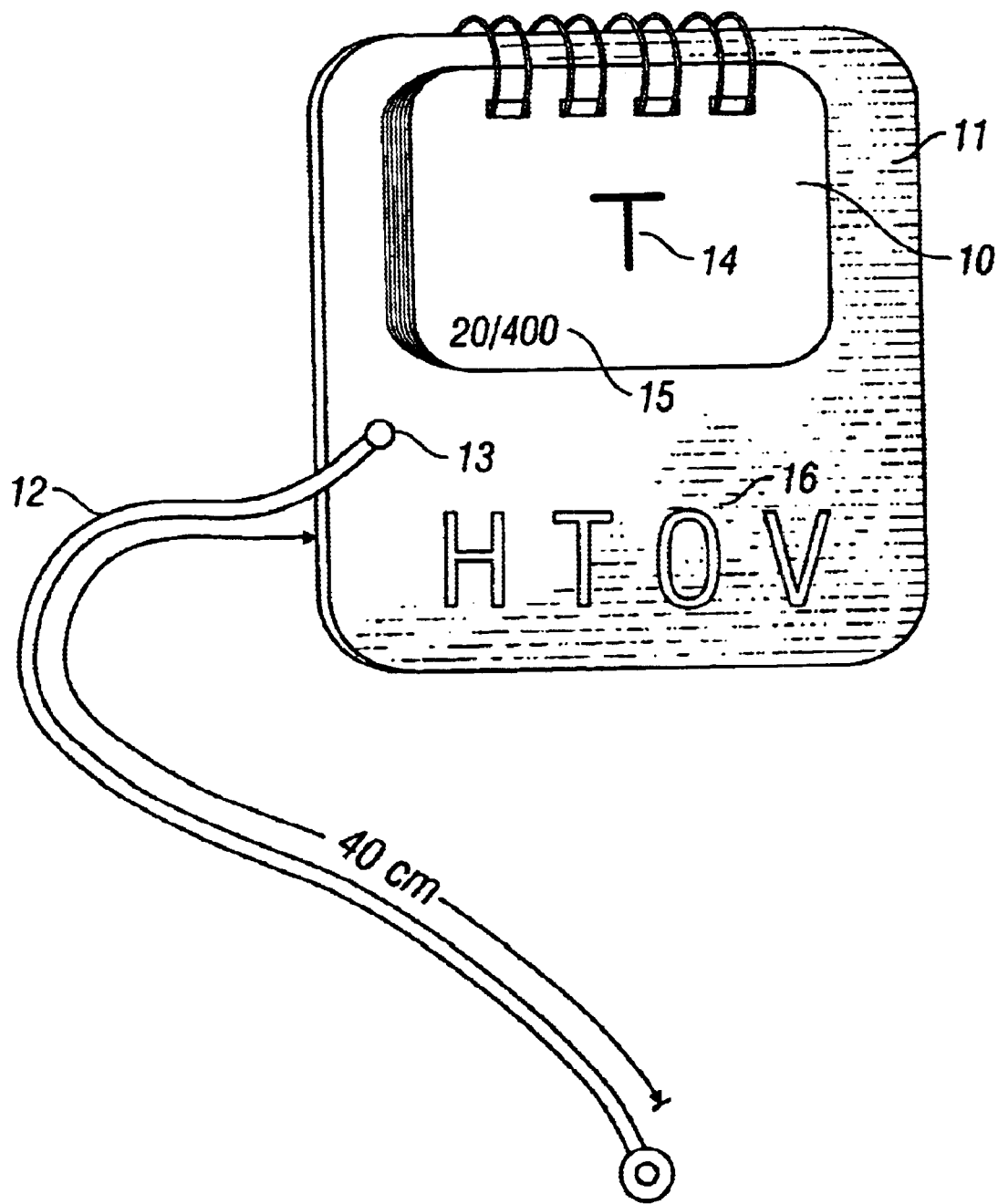
FIG. 1 is a representation of an apparatus for performing the Near Acuity test in the prior art.
Figure 2:
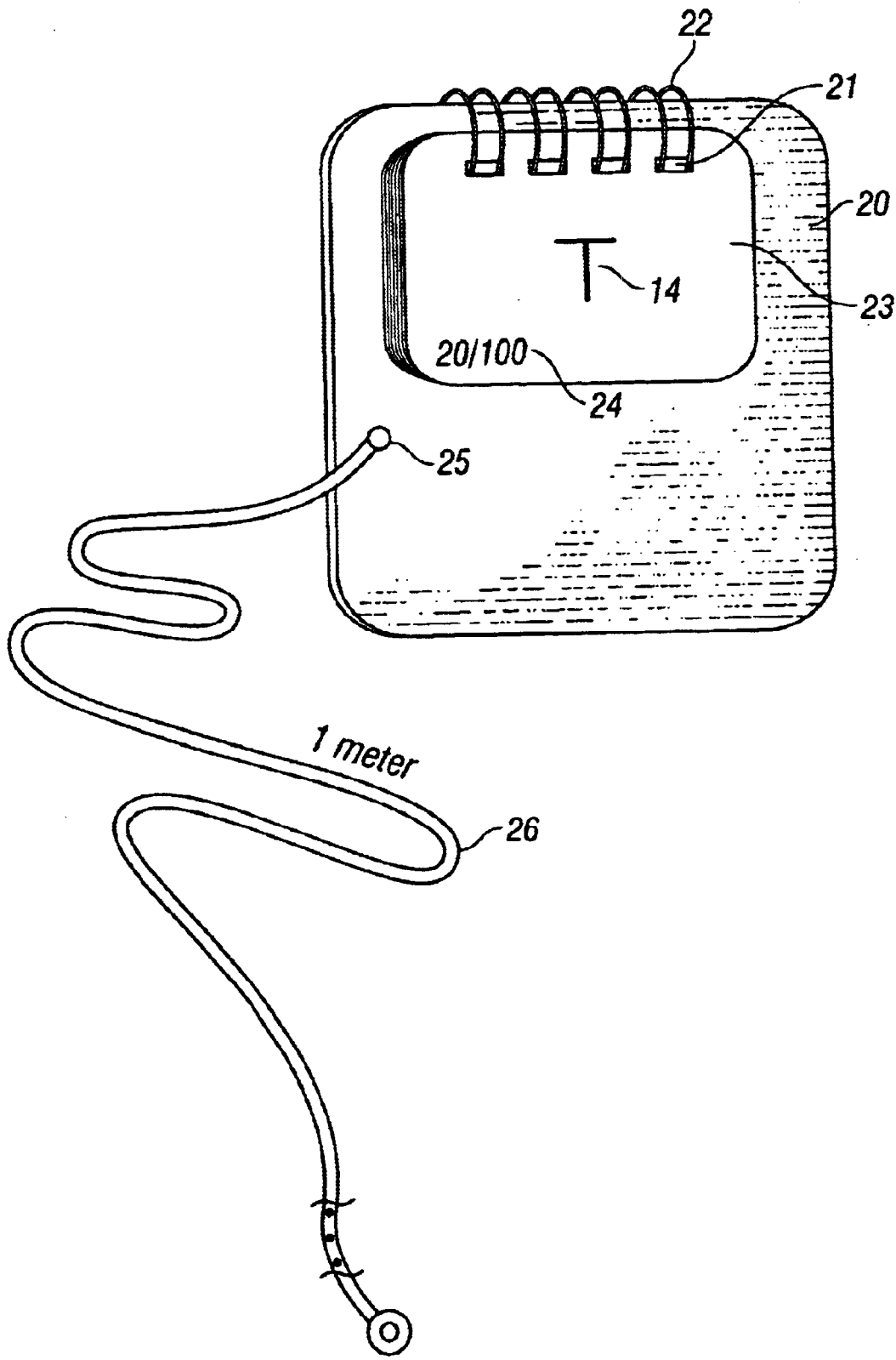
FIG. 2 is a representation of a vision screening apparatus according to an embodiment of the present invention.

FIG. 2 is a representation of a portable vision screening apparatus according to an embodiment of the present invention. The apparatus includes a base 20, having a series of holes 21 for receiving a spiral binder 22. The binder 22 loosely fastens a series of display cards 23 to the base 20 as a flip chart. The base also includes a hole 25 for connecting a string 26 of a predetermined length to the apparatus. In the preferred embodiment, the string is approximately one meter in length, to measure a patient's distance vision. Without departing from the scope of the invention, the string can be greater or less than one meter in length, although it cannot be sufficiently short so as to only enable the examiner to measure near acuity. For example, the string can be a length of between approximately 2.5' to 5', if the size of the optotypes on the display cards are properly calibrated to the string length.

The display cards each contain an optotype imprinted on each side of the card. The optotypes on one side of the card are known as "HOTV optotypes" (developed by Otto Lippmann, MD), which each include one of the following letters: "H", "O", "T", or "V". On the other side, the optotypes include one of the Lea symbols (a set of known symbols designed by Lea Hyvarinen, M.D., of Espoo, Finland, which adhere to recommendations of the visual acuity measurement standard set by the International Council of Ophthalmology (ICO)). The cards are arranged in the flip chart in a progression of increasingly smaller-sized optotypes, calibrated to provide an assessment of visual acuity (e.g., 20/100, 20/50, 20/30, etc.) according to the predetermined distance between the chart and the child's eye when in use. In the preferred embodiment, there are four cards per vision level, each displaying a different optotype at the same size.

Figure 6A:
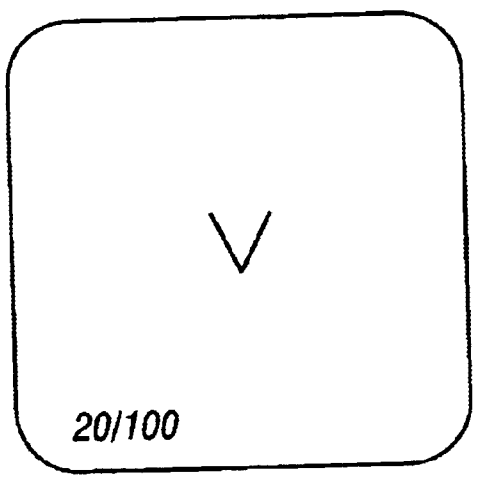
FIG. 6 is a representation of optotypes of the same type and different size on display cards of the vision screening apparatus of FIG. 2.
Figure 6B:
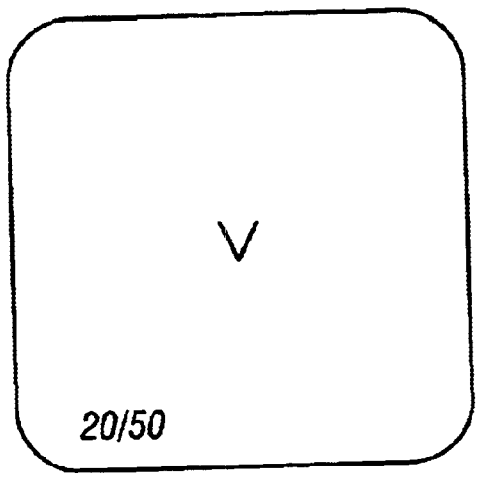
Figure 6C:
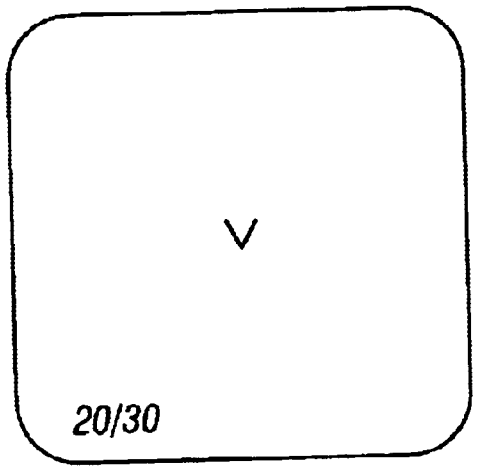
Figure 7A:
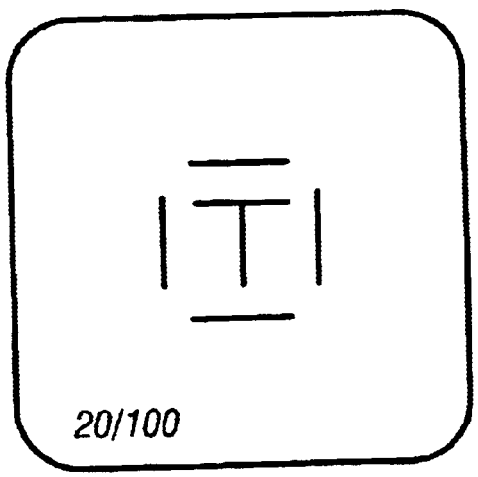
FIG. 7 is a representation of optotypes with surround borders, for use in the vision screening apparatus of FIG. 2.
Figure 7B:
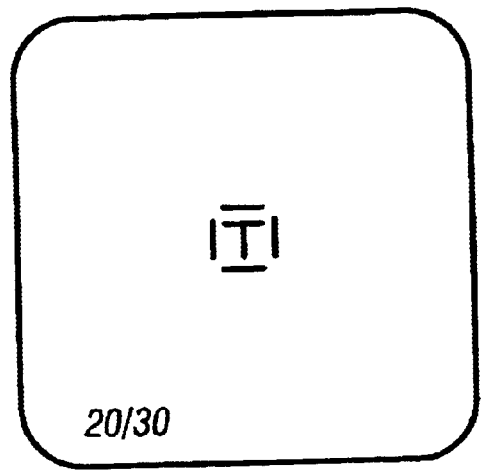

FIGS. 4–7 provide representations of the optotypes imprinted on the display cards. FIGS. 4 and 5 illustrate the progression of increasingly smaller-sized optotypes to provide an assessment at the 20/100, 20/50, and 20/30. FIG. 6 illustrates the same optotype, "V", at three different sizes. As can be seen in FIG. 4, the optotypes on display card "B" and "E" are the same type, but are different sizes to provide an assessment of a child's visual acuity at the 20/100 and 20/50 level, respectively. If, for example, it is detected that a child is able to identify optotypes that are sized at 20/100, but not the optotypes at 20/50, then the examiner may be able to draw a conclusion concerning the child's visual acuity. FIG. 7 provides a representation of a display card with "surround bars" around the optotype. Although it is not illustrated, it is also possible to display optotypes on a surface with a colored background to screen a patient's vision for contrast sensitivity.

Figure 3:
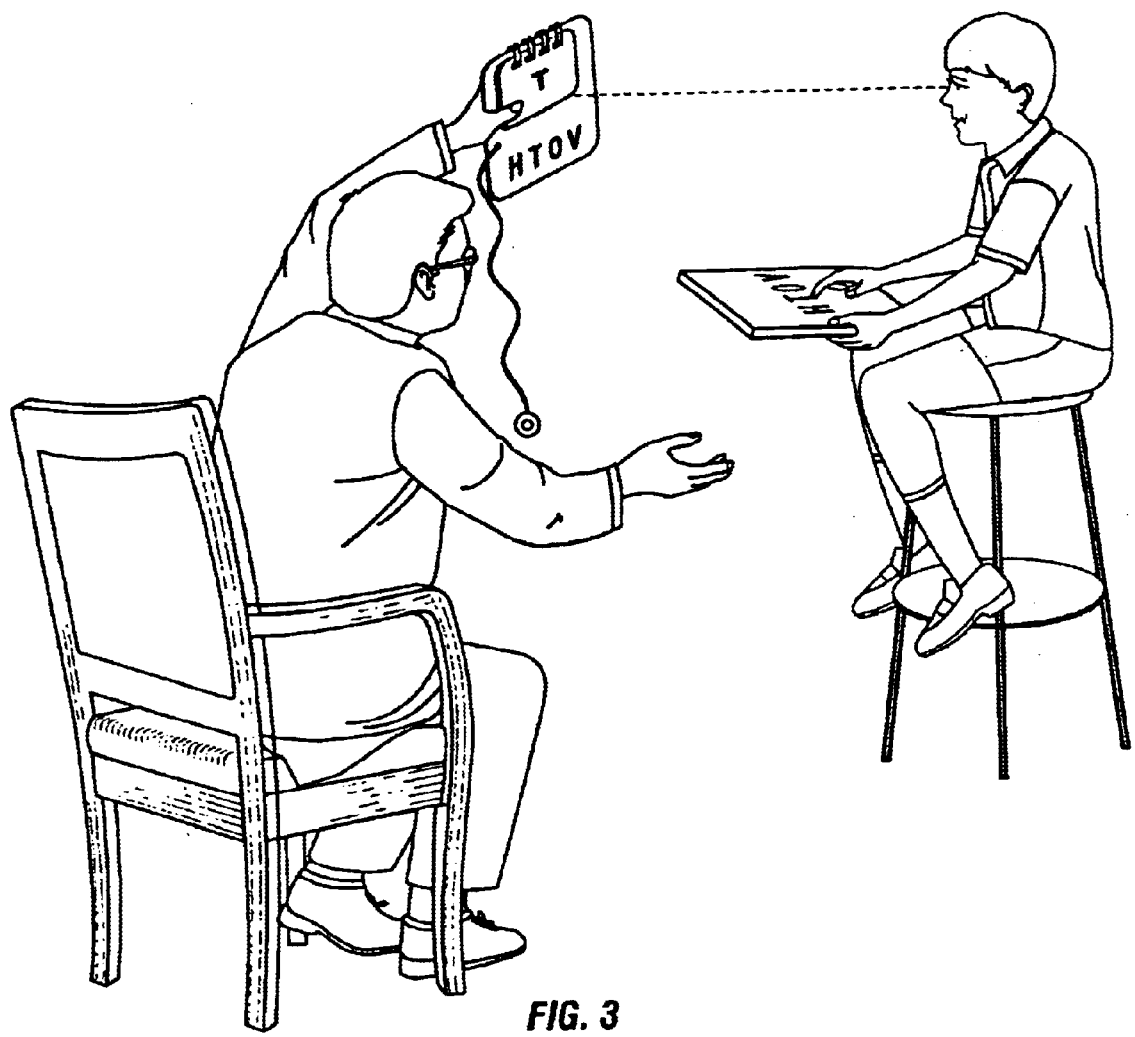
FIG. 3 is a representation of the method for utilizing the vision screening apparatus of FIG. 2 according to an embodiment of the present invention.
Figure 4A:
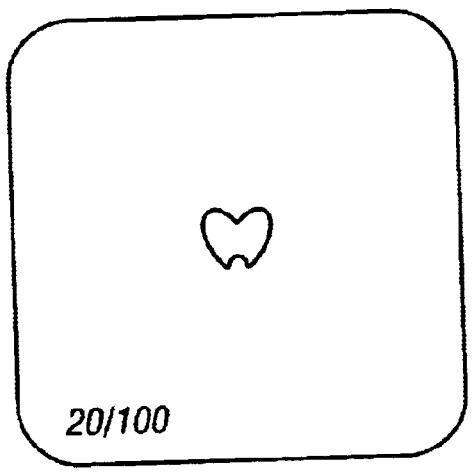
FIG. 4 is a representation of optotypes on display cards of the vision screening apparatus of FIG. 2.
Figure 4B:
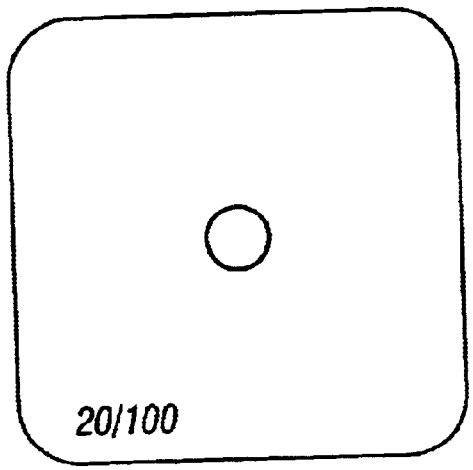
Figure 4C:
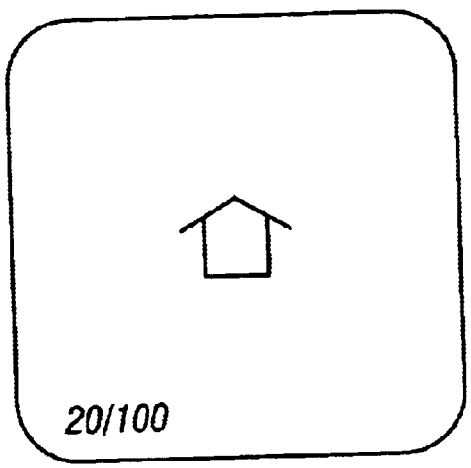
Figure 4D:
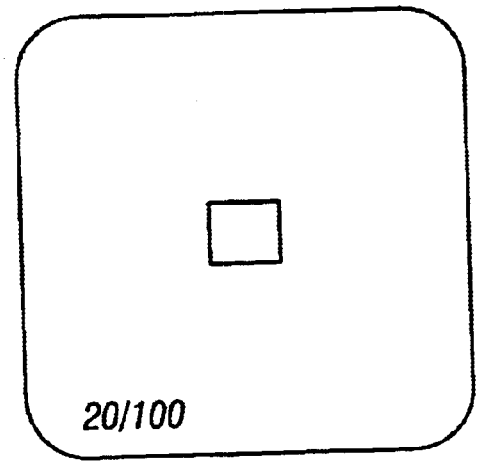
Figure 4E:
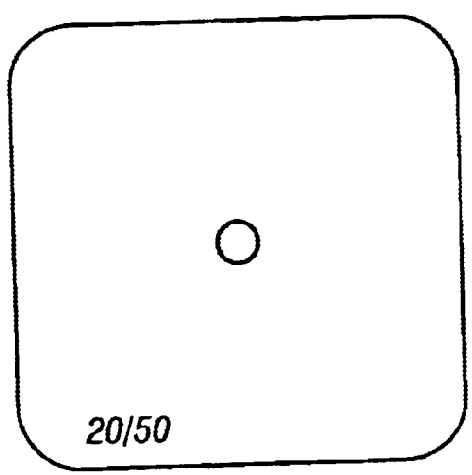
Figure 4F:
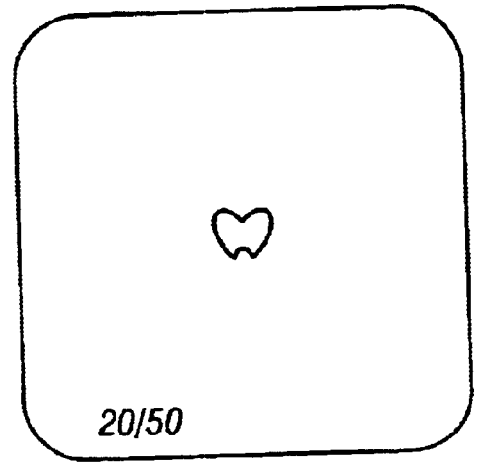
Figure 5A:
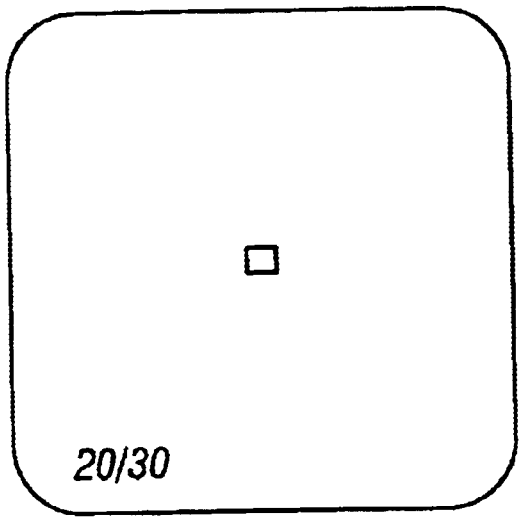
FIG. 5 is a representation of optotypes on display cards of the vision screening apparatus of FIG. 2.
Figure 5B:
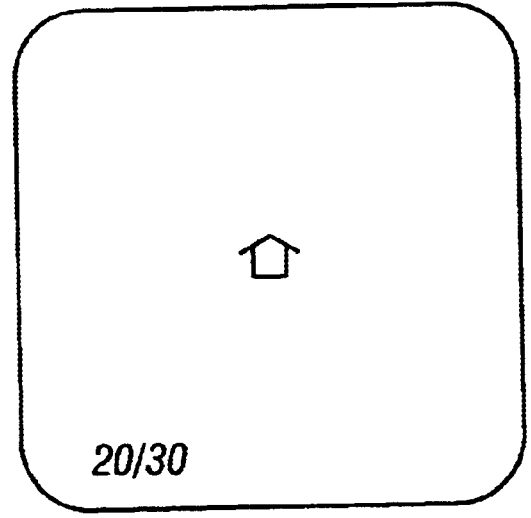
Figure 5C:
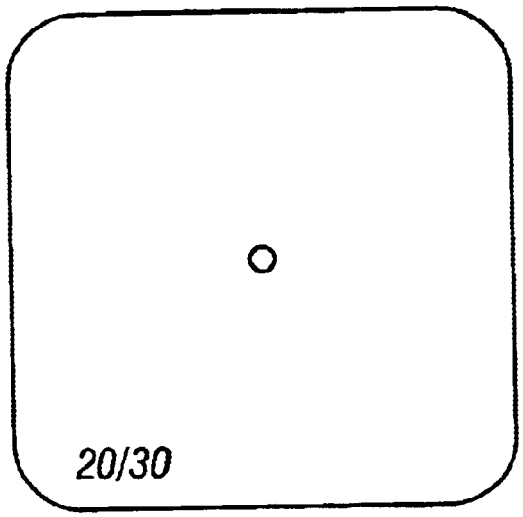
Figure 5D:
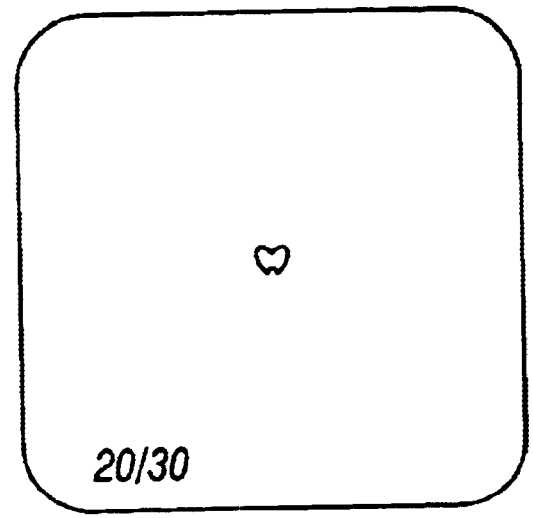

FIG. 3 provides a representation of a method for using the apparatus of FIG. 2 to screen the vision of a child of pre-school age for amblyopia. An examiner places the distal end of the string 26 near the child's eyes, and straightens the string by positioning the apparatus away from the child. Once the string is straight, the apparatus is correctly positioned, and the examiner can drop the string if he chooses to do so.

As can be seen in FIG. 3, an examiner (on the left) sits or stands at a close distance to the child (on the right), and holds the apparatus at the predetermined distance from the child's eyes. In this position, the examiner can easily monitor the child. With one hand, the examiner continues to hold the apparatus, while flipping through the flip chart with the other hand. The child is shown a series of cards on the flip chart, one at a time, and is asked to identify what is displayed on each card. The physician can use the string to periodically re-measure the distance between the child and the string to maintain a constant distance during the examination. In this embodiment, the cards are shown to the child at a distance of one meter. The child may sit in the lap of the child's parent (not shown) with the reference card in their lap.

The child is told that the physician and child are going to "play a matching game," whereby the child is to match each optotype that is displayed on a display card with the corresponding optotype on the reference card. With both eyes open, using the 20/100 optotypes to assure test aptitude, the child performs the matching exercise.

The child is then instructed to cover one eye. In the preferred embodiment, this is done by placing an orthoptic adhesive eye patch over the eye, although other techniques can also be used. One eye at a time, the child is then formally tested at the 20/100, 20/50, and 20/30 levels. A correct response for three out of four optotypes are needed to proceed to the next level. Vision of 20/30 is needed with each eye to pass. In other words, if the child is able to identify three out of four of the optotypes that are sized and calibrated at the 20/30 level, then significant amblyopia in that eye is not present.

Figure 8:
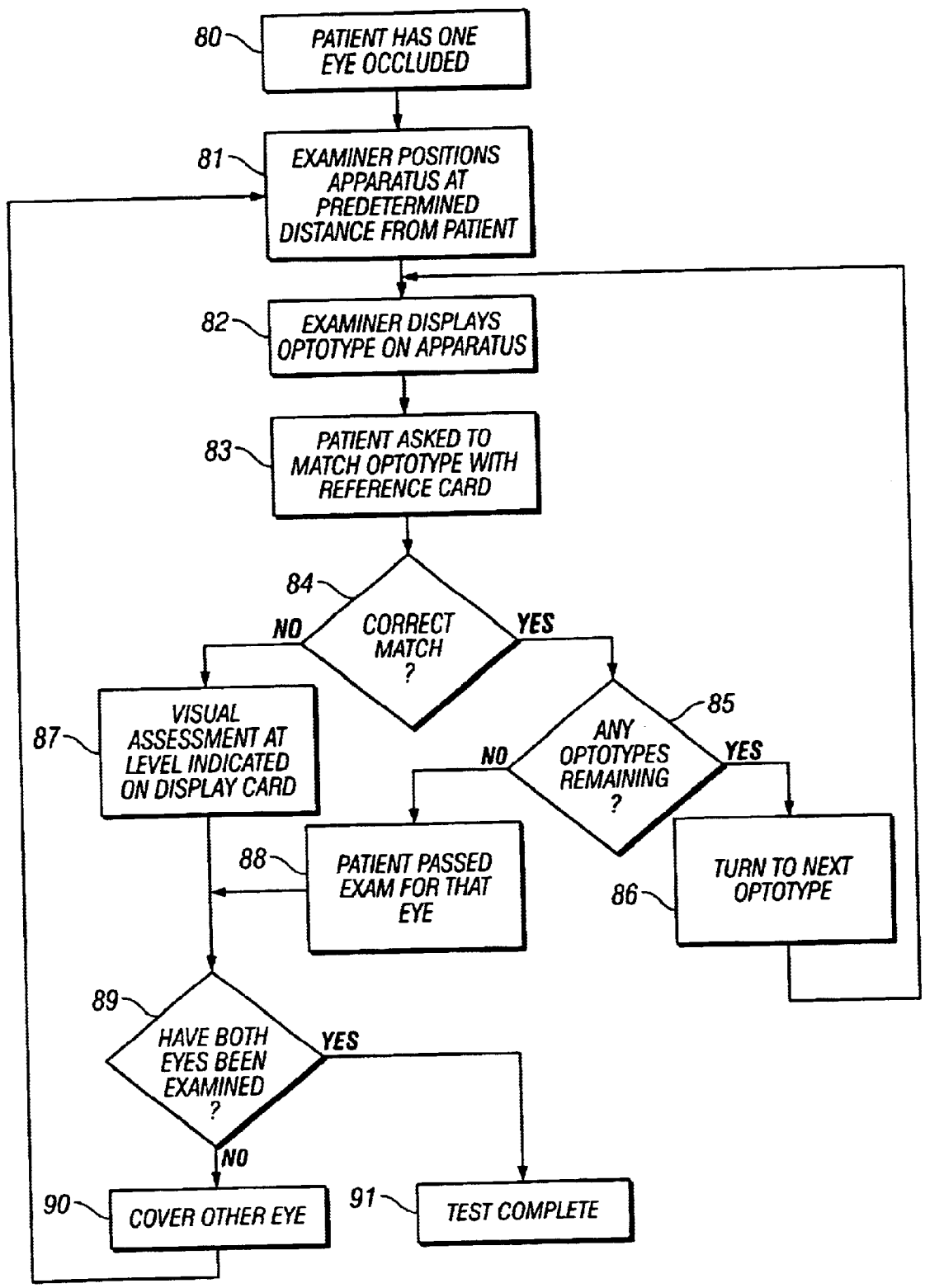
FIG. 8 is an exemplary flow diagram of a method for screening vision according to an embodiment of the present invention.
Figure 9:
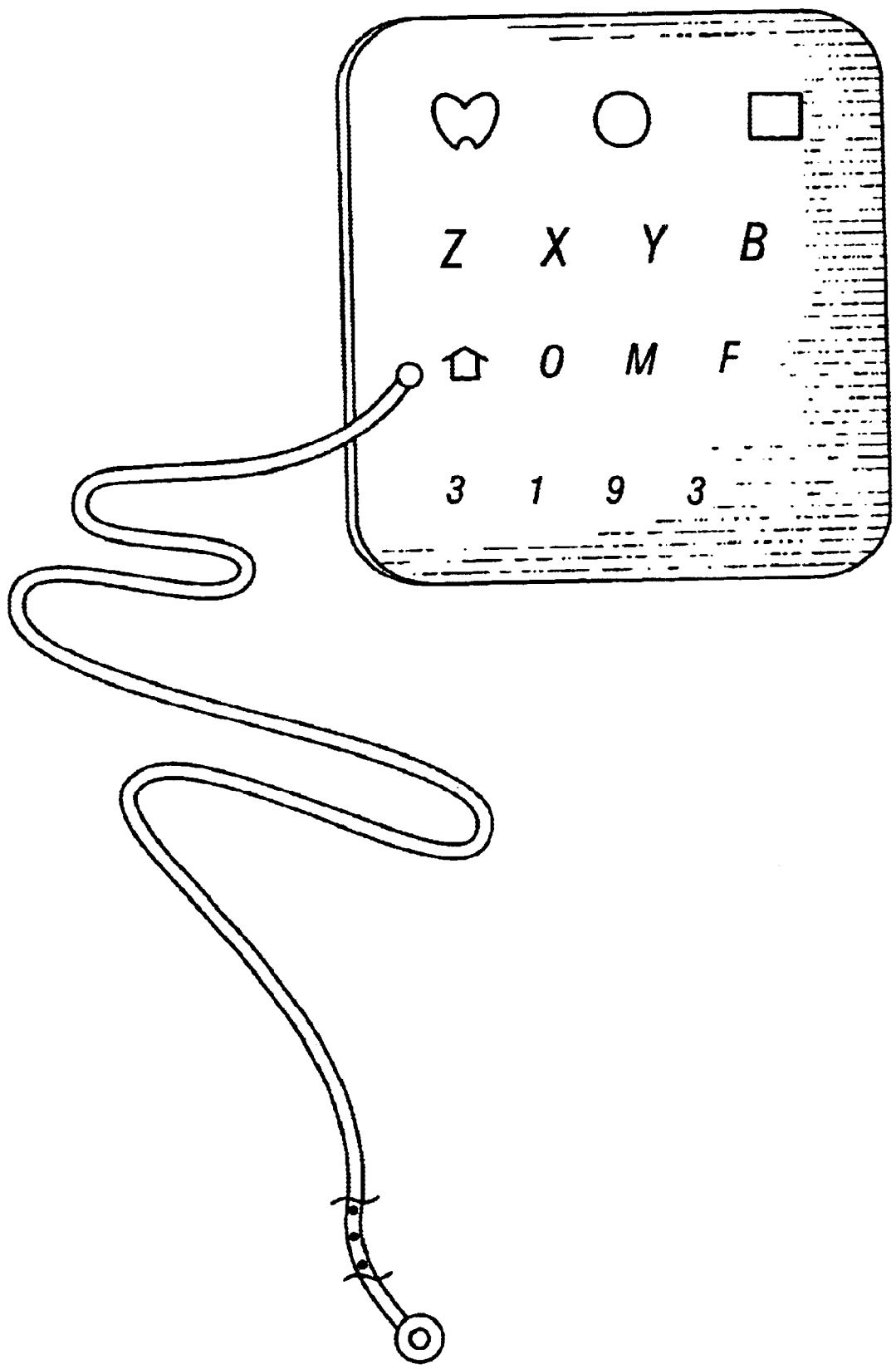
FIG. 9 is a representation of a vision screening apparatus according to an alternative embodiment of the present invention.

The method for screening vision using the portable vision screening apparatus of FIG. 2 is now described with reference to the flow diagram in FIG. 8. One of the patient's eyes is covered, in step 80. If a young child is being examined, the examiner (or the child's parent) can assist the child in covering one eye. By affixing an adhesive eye patch over the one eye, the child's hand will be freed to enable the child to hold a reference card and point to matching optotypes on the card, as described below.

Once the child is ready to begin the examination, the examiner positions the portable apparatus at a predetermined distance from the patient, in step 81. As described above, the string of predetermined length can be used to measure the appropriate length between the apparatus and the child, although any other method can also be used to accomplish this purpose, including the use of a tape measure or a meter stick, or an electronic distance sensor. The portable apparatus can also be affixed to a movable stand, which can be adjusted to be the appropriate, predetermined distance from the patient's eyes. In the preferred embodiment, the predetermined length is approximately one meter.

After positioning the apparatus, the examiner displays an optotype on a display card for the patient to identify, in step 82, and the patient is asked to match the optotype with a corresponding optotype on a reference card, in step 83. The patient may hold the reference card with one hand, or balance the card on the patient's lap. The reference card may also be affixed to a movable stand, positioned to be within arm's reach to allow the patient to point to the matching optotype. Because the reference card is to either be held by the patient, or held in the patient's lap, the patient will not need to move or otherwise shift her position in order to identify the optotypes with the reference card. This allows the examiner to easily continue the examination, without having to remeasure the distance between the display card and the patient.

If the patient correctly matches the optotype, in step 84, and there are other optotypes to be displayed, in step 85, then the examiner turns to the next optotype in step 86, and repeats the process, beginning in step 82. If the patient is unable to match the optotype, then a visual assessment is determined for that eye, according to the indicator on the display card (e.g., 20/100, 20/50, 20/30), in step 87 (e.g., failure to identify an optotype at 20/50 indicates visual assessment at or near that level.)

If the patient correctly matches all displayed optotypes, then the patient has passed the exam for that eye, in step 88. If the other eye has not yet been tested, in step 89, then the patient is instructed to cover the other eye in step 90, and the process is repeated, at step 81, until both eyes are tested, in step 91.

The portable vision screening apparatus as described can be provided as part of a compact vision screening kit for easy use by a primary care physician, nurse, or parent. The dimensions of the vision screening apparatus depicted in FIG. 2, which includes a base, a series of display cards fastened to the base through a binder, and a one meter length string, can be sized to fit within a small box, approximately 8 in. by 8 in. by 2 in. The box can also contain the reference card (sized at approximately 8 in. by 8 in.), and instruction sheet, and a set of eye patches.

While the reference card is particularly useful for examining pre-school age children, the reference card may be useful for examining any patient who is either unable who are unable to read or orally describe the optotypes on the display cards. Particularly, the reference card may be useful in examining patients who are mentally retarded or unable to speak. Conversely, it is not required for the patient to point to the matching optotype on a reference card if the patient is able to orally identify the optotype. For example, if a child recognizes the letter "T", the child can simply tell the examiner the letter, instead of pointing to a chart.

Several alternative embodiments are possible without departing from the present invention. For example, instead of using a flip chart apparatus as shown in FIG. 2, all optotypes, in varying sizes, may be displayed on a single display. Although the chart may appear much like a conventional eye chart, the size of the optotypes are calibrated in size to be read from a much closer distance, to enable the examiner to easily monitor the patient's responses while pointing to optotypes on the chart.

The optotypes can also be displayed on a portable, computer-controlled screen, such as a flat panel or liquid plasma display, or an LCD, where the display is calibrated to display optotypes at certain sizes appropriate for a patient to view at a distance of approximately one meter. If the computer-controlled display is affixed to a stand, the examiner can utilize a remote controller to change the display of optotypes on the screen.

As shown and described, the vision screening apparatus and method provides a portable, inexpensive, uncomplicated, and effective method to screen vision for vision disorders. In the foregoing detailed description, systems and methods in accordance with embodiments of the present invention have been described with reference to specific exemplary embodiments. Accordingly, the present specification and figures are to be regarded as illustrative rather than restrictive.

What is claimed is:

1. A method for conducting a vision examination by an examiner to screen a patient for vision disorders, comprising the steps of:

(a) positioning a display medium at a predetermined distance from a patient's eyes, wherein the display medium displays optotypes of different sizes to provide an indication of visual acuity at one of a plurality of vision levels, and wherein the sizes of the optotypes are calibrated for display at the predetermined distance;

(b) individually presenting a plurality of optotypes from a set of optotypes for the patient to view from the predetermined distance; and (c) for each optotype displayed to the patient, requesting the patient to find a matching optotype on a reference card, wherein a correct match indicates that the patient is able to see the optotype on the display medium.

2. The method of conducting a vision examination according to claim 1, further comprising the step of using a string attached to the display medium to measure a predetermined distance for positioning the display medium at the predetermined distance from the patient's eyes.

3. The method of conducting a vision examination according to claim 1, wherein the predetermined distance is approximately one meter.

4. The method of conducting a vision examination according to claim 1, wherein the examination is conducted with one eye covered at a time, and the predetermined distance is sufficient to screen a child's vision for amblyopia.

5. The method of conducting a vision examination according to claim 1, wherein the set of optotypes includes four optotypes for each particular vision level, and the patient is screened for each particular vision level by correcting matching at least three out of four optotypes for that vision level.

6. The method of conducting a vision examination according to claim 5, wherein the patient can be screened for amblyopia by determining whether the patient can correctly match at least three out of four optotypes at a vision level of 20/30.

7. A method of conducting a vision examination by an examiner to screen a patient for vision disorders, comprising the steps of:

(a) measuring a predetermined distance from the patient, wherein the predetermined distance is sufficient to evaluate distance vision;

(b) positioning a set of display cards at the predetermined distance from the patient's eyes, wherein each display card contains an optotype of a size calibrated for display at the predetermined distance, and wherein the optotypes are of different sizes to provide an indication of visual acuity at one of a plurality of particular vision levels;

(c) selecting a display card from the set of display cards;

(d) displaying the selected display card and requesting the patient to identify the optotype on the display card; and (e) receiving an attempted identification of the optotype from the patient, wherein the steps (c), (d), and (e) are repeated until a sufficient number of optotypes have been displayed to screen the patient for a particular vision disorder.

8. A vision screening apparatus for use by an examiner for screening vision in a patient to detect vision disorders, comprising:
- (a) a display medium for displaying optotypes of varying sizes, calibrated to indicate an assessment of visual acuity, wherein the display medium is to be positioned at a predetermined distance from the patient; and
- (b) a reference card displaying a set of optotypes corresponding to the optotypes provided on the display medium, to be positioned at a close distance from the patient to enable the patient to point to an optotype on the reference card that matches the optotype displayed on the display medium,
    wherein the predetermined distance is at least a minimum distance from the patient to measure distance vision, and is less than a maximum distance by which the examiner can be in close proximity to both the display medium and the reference card, and
    whereby the examiner monitors responses from the patient at the reference card to determine whether the patient is able to see the optotypes displayed on the display medium.

9. The vision screening apparatus according to claim 8, wherein the display medium further comprises a measuring device for enabling the examiner to position the display medium at the predetermined distance from the patient.

10. The vision screening apparatus according to claim 9, wherein the measuring device is a string of length equal to the predetermined distance.

11. The vision screening apparatus according to claim 9, wherein the measuring device is an electronic distance sensor.

12. The vision screening apparatus according to claim 8, wherein the predetermined distance is approximately one meter.

13. The vision screening apparatus according to claim 8, wherein the vision screening apparatus is portable.

14. The vision screening apparatus according to claim 8, wherein the predetermined distance is sufficient to enable the examiner to screen a child's vision for amblyopia.

15. A portable vision screening apparatus for use by an examiner for screening vision in a patient to detect vision disorders, comprising:
- (a) a series of display cards attached to a base as a flip chart, wherein each card displays an optotype calibrated to indicate an assessment of visual acuity at a particular vision level when viewed from a predetermined distance;
- (b) a string attached to the base having a length equal to the predetermined distance,
    wherein the predetermined distance is of at least a minimum length to measure distance vision to enable detection of vision disorders; and
- (c) a reference card displaying optotypes matching the optotypes provided on the display cards, whereby a patient points to the optotype on the reference card that corresponds with the optotype displayed on the display card.

16. The portable vision screening apparatus according to claim 15, wherein the predetermined distance is approximately one meter in length.

17. The portable vision screening apparatus according to claim 15, wherein the set of display cards contains four optotypes for each particular vision level, and the child is screened for each particular vision level by correctly matching on the reference card at least three out of four optotypes for that vision level.

18. The portable vision screening apparatus according to claim 17, wherein the vision levels include 20/100, 20/50, and 20/30.

19. The portable vision screening apparatus according to claim 15, wherein the predetermined distance is sufficient to screen a child's vision to detect amblyopia.

* * * * *